United States Patent
Mallard

[11] Patent Number: 6,085,591
[45] Date of Patent: Jul. 11, 2000

[54] IMMERSION TESTING POROUS SEMICONDUCTOR PROCESSING COMPONENTS

[75] Inventor: Richard L. Mallard, Pearl River, N.Y.

[73] Assignee: Tokyo Electron Limited, Tokyo, Japan

[21] Appl. No.: 08/124,332

[22] Filed: Sep. 21, 1993

[51] Int. Cl.[7] .................................................. G01N 29/00
[52] U.S. Cl. .................................. 73/627; 73/629; 73/644
[58] Field of Search ............................... 73/627, 629, 644

[56] References Cited

U.S. PATENT DOCUMENTS

| | | | |
|---|---|---|---|
| 3,929,006 | 12/1975 | Boggs et al. ............................... | 73/609 |
| 4,058,000 | 11/1977 | Ries et al. .................................. | 73/629 |
| 4,059,098 | 11/1977 | Murdock .................................... | 73/644 |
| 4,158,308 | 6/1979 | Sharpe et al. ............................. | 73/629 |
| 4,252,022 | 2/1981 | Hurwitz ..................................... | 73/644 |
| 4,653,504 | 3/1987 | Kondo et al. ............................. | 73/644 |
| 5,123,281 | 6/1992 | Cox et al. .................................. | 73/644 |
| 5,301,552 | 4/1994 | Nagura et al. ............................ | 73/629 |
| 5,406,849 | 4/1995 | Drescher-Krasicka et al. .......... | 73/627 |
| 5,406,850 | 4/1995 | Bouchard et al. ........................ | 73/629 |

FOREIGN PATENT DOCUMENTS

3337842A1   4/1984   Germany .

OTHER PUBLICATIONS

Lantukh, V.M., "Austenitic steel weld seam tester" WPI Database, Derwent Publications Inc., AN–298090 no date.

Prokhorenk, P.P. et al., "Ultransonic articles processing tank . . . " WPI Database, Derwent Publications Inc., AN 85–054626 no date.

"Ultrasonic Inspection", ASM Committee on Ultrasonic Inspection pp. 161–163, 173–174, 181, 387 no date.

"The Measures of Performance in Thin Film Materials", TOSOH SMD, Inc. (12 pages) no date.

FTS Mark IV Flaw Scope Operator's Manual, pp. 1–1, 1–2, 1–10 Staveley NDT Technologies, Trenton, NJ 08639 no date.

*Primary Examiner*—Eric S. McCall
*Attorney, Agent, or Firm*—Wood,Herron&Evans,L.L.P.

[57] ABSTRACT

To permit immersion ultrasonic testing of a semiconductor processing component manufactured of porous metal, a cover is sealed over the processing surface of the component. The cover creates an acoustically reflective air gap between the cover and the processing surface. Ultrasonic waves scanned across the component reflect from this gap, creating an image of the internal structure of the component.

12 Claims, 2 Drawing Sheets

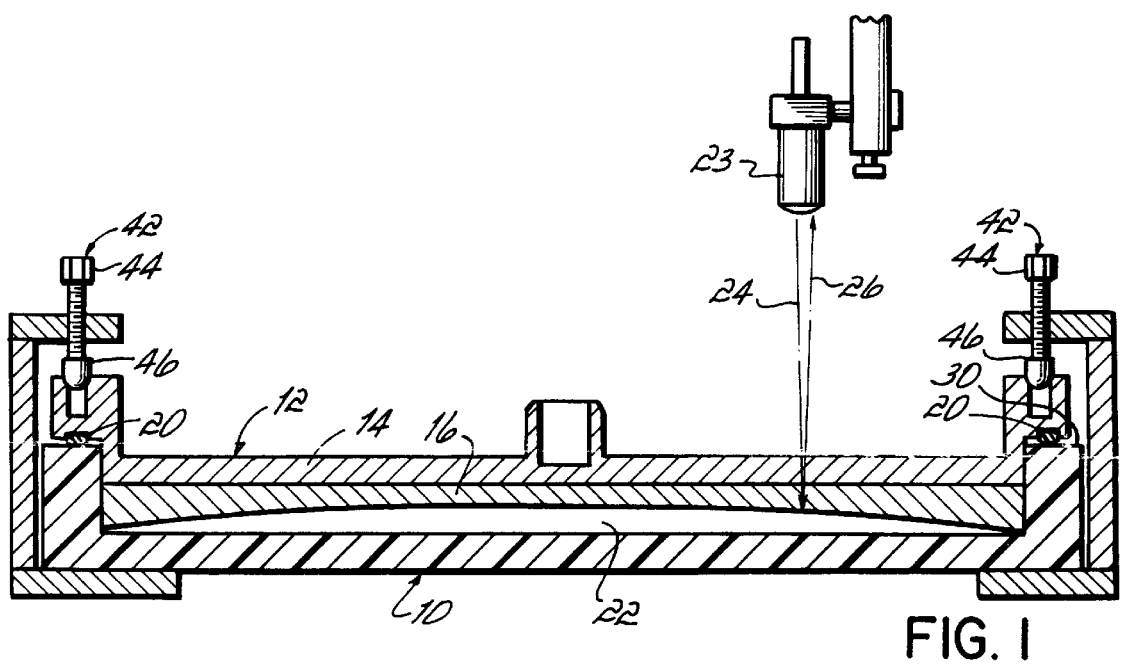
FIG. 1
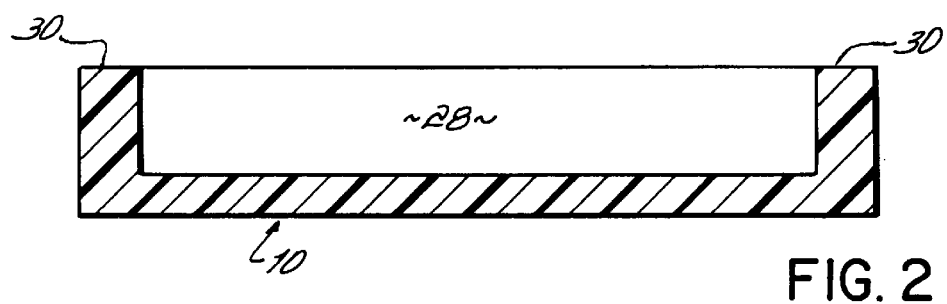
FIG. 2
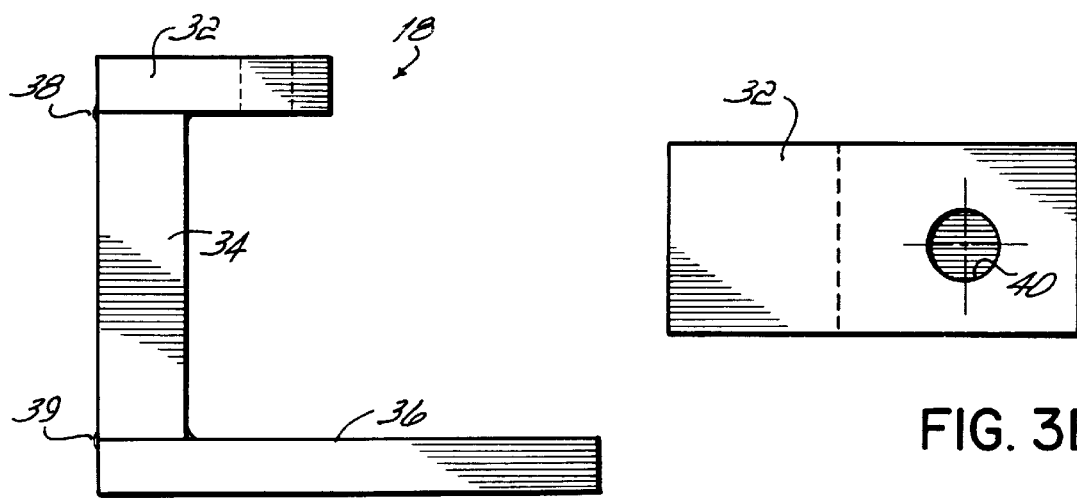
FIG. 3A
FIG. 3B

IMMERSION TESTING POROUS SEMICONDUCTOR PROCESSING COMPONENTS

BACKGROUND OF THE INVENTION

The invention relates to testing of semiconductor fabrication components.

High-precision manufacturing components are often tested for defects by manufacturers and consumers. Testing is most necessary where raw materials are expensive. Thus, for example, components used in semiconductor processing are frequently tested because the raw materials used in semiconductor manufacturing (new and partially processed wafers) are expensive.

Various techniques are available for testing the integrity of semiconductor processing components. One technique is x-ray radiography; in this technique the component is placed between an x-ray source and a sheet of photographic paper. The resulting image on the photographic paper can be used to detect voids in the manufactured component. A difficulty with this technique is that it does not detect other types of flaws in the component, e.g., cracks and other mechanical flaws in welds. Another difficulty with this technique is that it requires elaborate physical manipulation of the component and photographic paper to obtain a useful image, and therefore is difficult to implement as an automated operation on a production line.

A second testing technique is ultrasound testing; in this technique an ultrasonic transducer which generates ultrasonic energy is coupled to the component; ultrasonic energy reflected within the component is received by the transducer. A 2- or 3- dimensional CRT image of the internal structure of the component can be generated by moving the transducer into various locations across the surface of the component. The resulting image can be used to evaluate the strength of welds or other bonds in the component as well as locate voids or other imperfections.

Ultrasound testing (UT) requires acoustic coupling between the ultrasonic transducer and the object under test. In contact UT, the transducer is firmly pressed against the object under test as the transducer travels across the surface of the component. A difficulty with this technique is that a relatively sophisticated control procedure must be used to maintain tight contact between the component and the transducer as the transducer follows the surface of the component. This can make it difficult to implement contact UT as an automated operation on a component production line.

Immersion UT avoids this difficulty by immersing the component under test in a tank of liquid (typically, water). Ultrasonic energy can then be coupled into the component without making physical contact between the component and the ultrasonic transducer. Because immersion UT does not involve elaborate or precise physical manipulation of the component, it is relatively easier to implement as an automated operation on a component production line.

A difficulty with immersion UT is that the immersion liquid may react with and contaminate the surface of the immersed component, particularly where the component is manufactured of a "porous" material (e.g., Tungsten, Titanium, Iron, Terbium, Cobalt, Copper). Semiconductor manufacturing components such as sputtering targets are often made of such porous materials and therefore cannot be tested using immersion UT.

SUMMARY OF THE INVENTION

In one aspect, the invention features a method and apparatus for protecting a processing surface of a manufactured semiconductor component to permit immersion ultrasonic testing of the component. A cover plate is engaged to the component and sealed over the processing surface of the component, forming an acoustically reflective volume between the cover and the processing surface. Ultrasonic energy impinging on the component is reflected from this volume, collected, and used to generate an ultrasonic image of the component.

In preferred embodiments, the component is a sputtering target and the reflective volume is an air gap between the target and cover. The target and cover are typically disk-shaped, the target having a substantially concave processing surface and the cover having a substantially flat surface. The cover is engaged to the target by C-shaped clamps.

BRIEF DESCRIPTION OF THE DRAWING

The above features will be more clearly understood with reference to the following description and accompanying drawings, of which:

FIG. 1 is a cross-sectional view of a cover 10 clamped to a target 12 of porous material by clamps 18 to permit immersion UT by transducer 23;

FIG. 2 is a detail view of cover 10 of FIG. 1;

FIG. 3A is a detail view of clamp 18 of FIG. 1;

FIG. 3B is a detail of section 32 of clamp 18 of FIG. 3A;

DESCRIPTION OF THE PREFERRED EMBODIMENTS

Figure 3C:
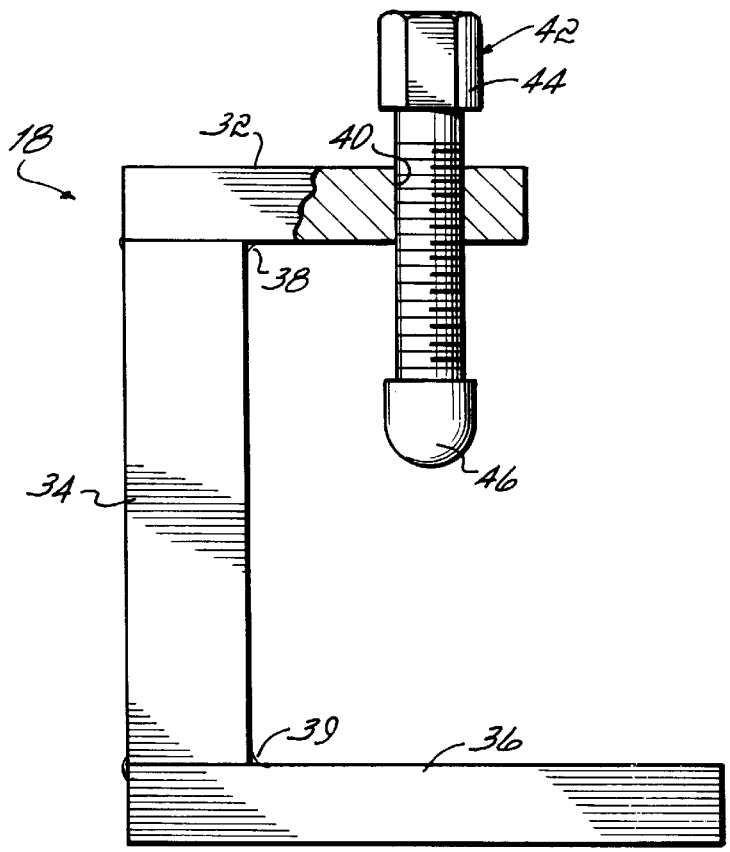
FIG. 3C is a detail of clamp screw 42 of FIG. 1.

As illustrated in FIG. 1, a cover 10 in accordance with the invention is sized to fight tightly over a processing surface of a processing component to be protected during immersion UT. In the embodiment illustrated in FIG. 1, the processing component is a target 12 for use in a sputtering chamber (specifically, a target marketed by Materials Research Corporation of Orangeburg, N.Y. under the trademark "RMX10", designed for use in processing chambers marketed by Materials Research Corporation under the trademark "ECLIPSE").

Target 12 comprises a metal backplate 14 laminated to a front section 16 of porous material (e.g., Tungsten, Titanium, Iron, Terbium, Cobalt, Copper). When the target is used to process wafers, front section 16 is placed in proximity to a wafer within a plasma processing chamber. Material is sputtered from front section 16 and deposits on the wafer, creating circuit elements on the wafer.

Cover 10 is clamped to target 12 by clamps 18. In one embodiment, cover 10 and target 12 are circular in shape, and four clamps 18 are arranged in approximately equal spacing around the perimeter of the target and cover to maintain tight contact (see, e.g., FIG. 4). An O-ring 20 placed between the cover 10 and target 12 forms a watertight seal, protecting the front section 16 from exposure to immersion fluid during immersion UT. O-Ring 20 is preferably manufactured of rubber, such as rubber manufactured by E.I. duPont de Nemours & Co., Inc. of Wilmington, Del. and sold under the trade name "VITON".

An air cavity 22 is formed between the front section 16 of the target and the cover 10. In one embodiment, the front section 16 of target 12 has a concave curved surface, and cover 10 has a flat surface, resulting in an air cavity 22 which is thickest near to the center of the target, and thinner near to the edges of the target. However, the surface topographies of the component and cover are not critical to proper operation, so long as there is a cavity between the component and the cover when the cover is seated on the component, or another element serving as an acoustic reflector as described below.

FIG. 1 also illustrates a transducer unit 23 used for immersion UT positioned over the target/cover assembly. In one embodiment, transducer unit 23 is ultrasonic flaw/thickness scope sold under the trade name "FTS MARK IV" by Staveley NDT Technologies—Sonic Systems of Trenton, N.J., and is installed in an immersion tank manufactured by Automation/Sperry (a unit of QualCorp) of Chatsworth, Calif. Transducer 23 emits ultrasonic waves (e.g., 10 MHz waves), illustrated by ray 24, in the direction of the target/cover assembly.

Ultrasonic waves emitted by transducer 23 are carried by the immersion fluid and into the backplate 14 of the target. The waves are then carried through the target. Material imperfections, voids, cracks, or any other interfaces within the target (e.g., the interface between backplate 14 and front section 16) will reflect a portion of the ultrasonic wave energy entering the target. At the same time, at least a portion of the energy will carry fully through the target, and reach the boundary between the target front section 16 and cavity 22. The acoustic impedance of cavity 22 is substantially higher than that of the immersion fluid or target 12; as a result, ultrasonic wave energy reaching cavity 22 is nearly completely reflected back into the target. At least some of the wave energy from each of these reflections reflects in the direction illustrated by ray 26. These reflected waves travel back through the target 12, through the immersion fluid and into transducer 23. The magnitude and timing of the reflected waves are then processed to generate a two-dimensional image of the target, showing imperfections and material interfaces. Also, by scanning transducer 23 over the target, two-dimensional data gathered at different locations can be combined to produce a cross-sectional image of the target (see FIG. 4). These techniques are further described in the operating instructions for the "FTS MARK IV" flaw scope (published by Staveley NDT Technologies) and/or in "Ultrasonic Inspection", available from the ASM Committee on Ultrasonic Inspection, both incorporated by reference herein.

FIG. 2 illustrates cover 10 with greater detail, including relevant dimensions. Cover 10 may be manufactured from a single sheet of Teflon (e.g., sold in 12 inch by 12 inch by 1.5 inch sections by U.S. Plastics of Lima, Ohio as stock number 47494), by turning the sheet on a lathe to form a solid cylinder (e.g., 11.060 inches in diameter and 1.42 inches thick), and then removing a cylindrical center section 28 (e.g., 0.92 inches deep and 10.020 inches in diameter). The resulting cover will fit snugly over the above-described target, leaving a cavity 22 to permit immersion UT imaging.

Surface 30 of cover 10 is smoothed to a roughness average value of 32 microinches (peak to trough), so that a tight seal can be formed between cover 10 and backplate 14 with O-ring 20.

FIG. 3A illustrates the construction of clamp 18; the clamp is formed of three sections of steel, e.g., sections cut from a steel bar having a rectangular 0.75 inch by 0.375 inch cross-section. Section 32 is 1.080 inches long; section 34 is 3.125 inches long; section 36 is 2.200 inches long. The sections are held together by 0.100 inch gas tungsten arc welds 38 and 39, formed using 0.062 inch filler at 300 Amps and 4.3% gas flow at 8 P.S.I..

Section 32 includes a threaded bore 40 which is tapped to accept a 0.25 inch—20 bolt which serves as a clamp screw (see below). As shown in FIG. 3B, the center of bore 40 is 0.300 inch away from the joint 38 between section 32 and section 34, thus providing sufficient clearance for a clamp screw.

The details of clamp screw 42 are visible in FIG. 3C. A 1.375 inch long, 0.25 inch—20 hexagonal head bolt 44 is threaded through bore 40. Then, a 0.25 inch—20 acorn nut 46 is screwed onto the end of bolt 44. Preferably, nut 46 is prepared by removing the hexagonal nut surfaces from a standard acorn nut (e.g., with a belt sander), leaving a nut 46 a smooth dome-shaped outer surface.

As seen in FIG. 1, with the above dimensions, the rounded surface of acorn nut 46 seats into existing bolt holes in the above-described target, thus achieving good clamping contact while minimizing damage to the backplate 14. Clamp screws 42 are torqued until O-ring compresses against the surfaces of cover 10 and target 12, approximately 11 foot-pounds of torque is needed. At this compression, the assembly can be immersed in a 100 gallon tank of water for five hours without detectible leakage.

Figure 4:
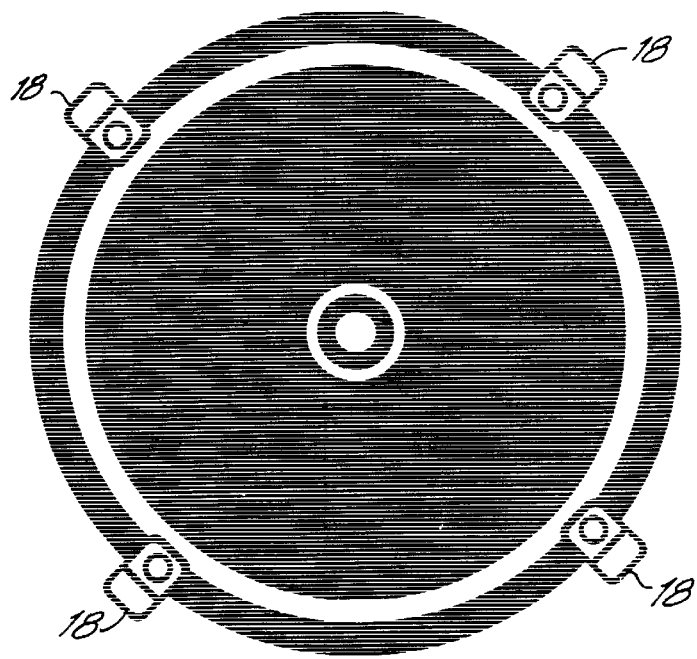
FIG. 4 is a print-out of an immersion UT scan performed with the apparatus of FIG. 1.

FIG. 4 illustrates the clear cross-sectional imaging possible with the immersion UT arrangement shown in FIG. 1. Transducer 23 was set to scan the target/cover assembly at 0.030 inch increments. Defects in the target 12 will appear as WHITE AREAS, and can be quickly located (there are no defects illustrated in FIG. 4). Furthermore, because immersion UT can be easily automated, components can be 100% tested at manufacturing facilities, and images such as FIG. 4 enclosed with the component packaging for customer assurance of quality.

The foregoing has described the invention with reference to a specific embodiment; however, various modifications may be made without departing from the disclosed inventive concepts. The specific embodiment described is to be taken as exemplary and not limiting.

What is claimed is:

1. A method for protecting a processing surface of a processing component while immersion ultrasonic testing said component, comprising
   positioning a front face of a cover plate and said processing surface of said component in confronting face-to-face relation,
   sealing a perimeter of said processing surface to said plate to form an acoustically reflective volume therebetween, while leaving exposed a non-processing surface of said component,
   impinging ultrasonic waves upon said non-processing surface of said component from a point external of said component to propagate said ultrasonic waves through said component and reflect said ultrasonic waves from said reflective volume,
   collecting ultrasonic waves reflected from said reflective volume, and
   generating an ultrasonic image of said component in response to said collected waves.

2. The method of claim 1 wherein said reflective volume is an air gap between said processing surface of said component and said cover front face.

3. The method of claim 1 wherein
   said processing surface and said cover front face are circular and
   said sealing step includes positioning a resilient circular seal between circular peripheral edges of said cover front face and said processing surface.

4. The method of claim 1 wherein said cover front face has a substantially flat topology, and said processing surface has a substantially concave topology.

5. The method of claim 1 wherein said sealing step includes clamping said cover to said component with one or more C-shaped clamps.

6. The method of claim 1 wherein said processing component is a sputtering target.

7. A cover plate comprising a front face, a back face, and a sealing rim at the a perimeter of said cover plate said cover establishing an acoustically reflective volume adjacent to said processing surface between said front face and said processing surface, said reflective volume reflecting ultrasonic waves entering said processing component and impinging on said processing surface from within said processing component.

8. The cover plate of claim 7 wherein said reflective volume is an air gap.

9. The cover plate of claim 7 wherein said processing surface, said front face and said back face are circular in shape.

10. The cover plate of claim 7 wherein said front face has a substantially flat topography, and said processing surface has a substantially concave topology.

11. The cover plate of claim 7 further comprising one or more C-shaped clamps for engaging said sealing rim to said processing component.

12. The cover plate of claim 7 wherein said processing component is a sputtering target.

* * * * *

UNITED STATES PATENT AND TRADEMARK OFFICE
CERTIFICATE OF CORRECTION

PATENT NO.     : 6,085,591                                        Page 1 of 1
DATED          : July 11, 2000
INVENTOR(S)    : Richard L. Mallard It is certified that error appears in the above-identified patent and that said Letters Patent is hereby corrected as shown below:

<u>Column 5,</u>
Line 10, reads "A cover plate comprising," and should read-A cover plate for attachment to a processing component for protecting a processing surface thereof during immersion ultrasonic testing, comprising--.

Signed and Sealed this

Fourteenth Day of August, 2001

Attest:

NICHOLAS P. GODICI
Attesting Officer      Acting Director of the United States Patent and Trademark Office